US006303306B1

(12) United States Patent
Takarada et al.

(10) Patent No.: US 6,303,306 B1
(45) **Date of Patent: *Oct. 16, 2001**

(54) METHOD FOR AMPLIFYING AND DETECTING OF TARGET NUCLEIC ACID SEQUENCE USING THERMOSTABLE ENZYME

(75) Inventors: Yutaka Takarada, Otsu; Hiroaki Inoue, Tsuruga; Shuji Shibata, Otsu; Yoshihisa Kawamura, Tsuruga, all of (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/292,435

(22) Filed: Apr. 15, 1999

Related U.S. Application Data

(62) Continuation of application No. 08/821,782, filed on Mar. 20, 1997, now Pat. No. 5,981,183, which is a continuation of application No. 08/446,709, filed as application No. PCT/JP94/02025 on Dec. 1, 1993, now abandoned.

(30) Foreign Application Priority Data

Dec. 1, 1993 (JP) ........................ 5-301823

(51) Int. Cl.[7] ........................ C12Q 1/68
(52) U.S. Cl. ........................ 435/6
(58) Field of Search ........................ 435/6, 91.2, 91.5, 435/41.51; 536/24.3, 24.32, 24.33

(56) References Cited

U.S. PATENT DOCUMENTS

| | | | |
|---|---|---|---|
| 4,683,195 | 7/1987 | Mullis et al. . | |
| 5,130,238 | 7/1992 | Malek et al. | 435/91 |
| 5,268,289 | 12/1993 | Dahl et al. | 435/199 |
| 5,322,770 | 6/1994 | Gelfand | 435/6 |
| 5,407,800 | 4/1995 | Gelfand et al. | 435/6 |
| 5,409,818 | 4/1995 | Davey et al. | 435/91.21 |
| 5,459,055 | 10/1995 | Jendrisak et al. | 435/199 |
| 5,981,183 * | 11/1999 | Takarada et al. | 435/6 |

FOREIGN PATENT DOCUMENTS

| | | | |
|---|---|---|---|
| 310229 | 4/1989 | (EP) | C12Q/1/68 |
| 598332 | 5/1994 | (EP) . | |
| 632683 | 11/1994 | (EP) | C12Q/1/68 |
| 632134 | 1/1995 | (EP) | C12Q/1/68 |
| WO 89/04374 | 5/1989 | (WO) | C12Q/1/68 |
| WO 91/01384 | 2/1991 | (WO) | C12Q/1/68 |
| WO 91/09944 | 7/1991 | (WO) | C12Q/1/68 |
| WO 92/08800 | 5/1992 | (WO) | C12Q/1/68 |
| WO 94/03472 | 2/1994 | (WO) | C12Q/1/68 |
| WO 94/05812 | 3/1994 | (WO) | C12Q/1/68 |

OTHER PUBLICATIONS

Date et al., *J. Biochem.*, 78, 845–858 (1975).
Fahy et al., *PCR Methods Appl.*, 1, 25–33 (1991).
Fahy et al., *PCR Methods Appl.*, 3, S83–S94 (1994).

(List continued on next page.)

*Primary Examiner*—Jeffrey Fredman
*Assistant Examiner*—Joyce Tung
(74) *Attorney, Agent, or Firm*—Leydig, Voit & Mayer, Ltd.

(57) ABSTRACT

In a method for amplifying the specific nucleic acid sequence, a highly specific amplification which has low possibility of non-specific hybridization can be carried out. Highly stable reagents, the activities of which do not decrease in case of supply and storage, are also provided. Thermostable enzymes are used as RNA dependent DNA polymerase, DNA dependent DNA polymerase, DNA dependent RNA polymerase and ribonuclease H, which are required for the amplification system based on replicated RNA. Especially, it is preferable that a thermostable enzyme derived from *Thermus thermophilus* which has RNA dependent DNA polymerase activity, DNA dependent DNA polymerase activity and ribonuclease H activity, and thermostable DNA dependent RNA polymerase are used together. By this method, inactivation of enzymes are prevented by using thermostable enzymes, and the amplification can be carried out without sequential addition of enzymes.

9 Claims, 5 Drawing Sheets

OTHER PUBLICATIONS

Gingeras et al., *J. Infect. Disease*, 164, 1066–1074 (1991).

Guatelli et al., *Proc. Natl.. Acad. Sci. USA*, 87, 1874–78 (1990).

Kanaya et al., *J. Biol. Chem.*, 267, 10184–10192 (1992).

Kievits et al., *J. Virol. Methods*, 35, 273–286 (1991).

Sooknannan et al., *Bio/Technology*, 13, 563–564 (1995).

Vandamme et al., *J. Virol Methods*, 52, 121–132 (Mar. 1995).

Walter et al., *Proc. Natl. Acad. Sci. USA*, 91, 7937–7941 (1994).

Zehbe et al., *Cell Vision*, 1, 20–24 (1994).

Zehbe et al., *Cell Vision*, 1, 46–47 (1994).

Zehbe et al., *Cell Vision*, 2, 240–242 (1995).

* cited by examiner

SEQUENCE LISTING

```
(1) GENERAL INFORMATION:

   (iii) NUMBER OF SEQUENCES: 35


(2) INFORMATION FOR SEQ ID NO: 1:

     (i) SEQUENCE CHARACTERISTICS:
          (A) LENGTH: 64
          (B) TYPE: nucleic acid
          (C) STRANDEDNESS: single
          (D) TOPOLOGY: linear
```

-continued (ii) MOLECULE TYPE: other nucleic acid (synthesized DNA)

(iii) FEATURE:
(A) NAME/KEY: promoter
(B) LOCATION: 1..30
(C) IDENTIFICATION METHOD: by similarity with known sequence or to an established consensus
(D) OTHER INFORMATION: promoter sequence (iii) FEATURE:
(B) LOCATION: 31..40
(C) IDENTIFICATION METHOD: by similarity with known sequence or to an established consensus
(D) OTHER INFORMATION: a spacer sequence containing a replication origin (iii) FEATURE:
(B) LOCATION: 41..64
(D) OTHER INFORMATION: having a sequence complementary to nucleotides 313-326 of TDH gene of Vibrio parahaemolyticus (iv) SEQUENCE DESCRIPTION: SEQ ID NO: 1:

```
CTTGACAAAA AGGAGGGGGA TTGATAGCAT GGCTTTTCTG GACACCGCTG CCATTGTATA     60

GTCT                                                                  64
```

(2) INFORMATION FOR SEQ ID NO: 2:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: other nucleic acid (synthesized DNA)

(iii) FEATURE:
(B) LOCATION: 1..24
(D) OTHER INFORMATION: having a sequence complementary to nucleotides 179-202 of TDH gene of Vibrio parahaemolyticus (iv) SEQUENCE DESCRIPTION: SEQ ID NO: 2:

```
CTGACTTTTG GACAAACCGT AATG                                            24
```

(2) INFORMATION FOR SEQ ID NO: 3:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: other nucleic acid (synthesized DNA)

(iii) FEATURE:
(B) LOCATION: 1..24
(D) OTHER INFORMATION: having a sequence complementary to nucleotides 254-277 of TDH gene of Vibrio parahaemolyticus (iv) SEQUENCE DESCRIPTION: SEQ ID NO: 3:

```
CAGGTACTAA ATGGTTGACA TCCT                                            24
```

(2) INFORMATION FOR SEQ ID NO: 4:

(i) SEQUENCE CHARACTERISTICS:
(A) LENGTH: 64
(B) TYPE: nucleic acid
(C) STRANDEDNESS: single -continued (D) TOPOLOGY: linear (ii) MOLECULE TYPE: other nucleic acid (synthesized DNA)

(iii) FEATURE:
(B) LOCATION: 1..30
(C) IDENTIFICATION METHOD: by similarity with known sequence or to an established consensus
(D) OTHER INFORMATION: promoter sequence (iii) FEATURE:
(B) LOCATION: 31..40
(C) IDENTIFICATION METHOD: by similarity with known sequence or to an established consensus
(D) OTHER INFORMATION: a spacer containing a replication origin (iii) FEATURE:
(B) LOCATION: 41..64
(D) OTHER INFORMATION: having a sequence complementary to nucleotides 179-202 of TDH gene of Vibrio parahaemolyticus (iv) SEQUENCE DESCRIPTION: SEQ ID NO: 4:

CTTGACAAAA AGGAGGGGGA TTGATAGCAT GGCTTTTCTG CTGACTTTTG GACAAACCGT 60

AATG 64

(2) INFORMATION FOR SEQ ID NO: 5:

(i) SEQUENCE CHARACTERISTICS:
(A) LENGTH: 22
(B) TYPE: nucleic acid
(C) STRANDEDNESS: single
(D) TOPOLOGY: linear (ii) MOLECULE TYPE: other nucleic acid (synthesized DNA)

(iii) FEATURE:
(B) LOCATION: 1..22
(D) OTHER INFORMATION: having a sequence complementary to nucleotides 483-504 of TDH gene of Vibrio parahaemolyticus (iv) SEQUENCE DESCRIPTION: SEQ ID NO: 5:

ACTACCACTC TCATATGCTT CT 22

(2) INFORMATION FOR SEQ ID NO: 6:

(i) SEQUENCE CHARACTERISTICS:
(A) LENGTH: 34
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 6:

CTTGACAAAA AGGAGGGGGA TTGATTGATA GCAT 34

(2) INFORMATION FOR SEQ ID NO: 7:

(i) SEQUENCE CHARACTERISTICS:
(A) LENGTH: 33
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 7:

-continued

TTCGCGCCCA TCGTACACCG AGGCGGTATC CTC 33

(2) INFORMATION FOR SEQ ID NO: 8:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 8:

CTTGACGGAG GCGGACGGCG CTGGTACACT 30

(2) INFORMATION FOR SEQ ID NO: 9:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 9:

CTGGACAGGG CCCCCGTGTC CCGCTATCCT 30

(2) INFORMATION FOR SEQ ID NO: 10:

(i) SEQUENCE CHARACTERISTICS:
(A) LENGTH: 31
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 10:

CTAGCCTCAG GGCTTCCATG GGTGCTATAC T 31

(2) INFORMATION FOR SEQ ID NO: 11:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 11:

CTTGACCCCG CAGGCCTCGA GGGCTTACCT 30

(2) INFORMATION FOR SEQ ID NO: 12:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 12:

CTTGACAAAA AGGAGGGGGA TTGATAGCAT 30

-continued (2) INFORMATION FOR SEQ ID NO: 13:

(i) SEQUENCE CHARACTERISTICS:
(A) LENGTH: 31
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 13:

CTTGACGCCG CCCAGGGCGG GCCTCTACCC T 31

(2) INFORMATION FOR SEQ ID NO: 14:

(i) SEQUENCE CHARACTERISTICS:
(A) LENGTH: 28
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 14:

TTTGAGGGCC TGGGGCAGTA CCTCTTCT 28

(2) INFORMATION FOR SEQ ID NO: 15:

(i) SEQUENCE CHARACTERISTICS:
(A) LENGTH: 28
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 15:

TTTGTAAAGT GCTTTATTTC ACAAAACT 28

(2) INFORMATION FOR SEQ ID NO: 16:

(i) SEQUENCE CHARACTERISTICS:
(A) LENGTH: 34
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 16:

TTTCACAAAA CTGTCCCTCC CCCCGGGTTA GACT 34

(2) INFORMATION FOR SEQ ID NO: 17:

(i) SEQUENCE CHARACTERISTICS:
(A) LENGTH: 29
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 17:

TTGACACTCT CGGGCGGGTG TGCTAGCCT 29

(2) INFORMATION FOR SEQ ID NO: 18:

(i) SEQUENCE CHARACTERISTICS:
(A) LENGTH: 30

-continued

```
(B) TYPE: nucleic acid
(C) STRANDEDNESS:  double
(D) TOPOLOGY:  unknown

(ii) MOLECULE TYPE: Genomic DNA

(iii) SEQUENCE DESCRIPTION:  SEQ ID NO: 18:

CTTGAGGATC TCGGGGAGGC GGGCTTCCAT                                    30


(2) INFORMATION FOR SEQ ID NO: 19:

(i) SEQUENCE CHARACTERISTICS:
(A) LENGTH: 29
(B) TYPE: nucleic acid
(C) STRANDEDNESS:  double
(D) TOPOLOGY:  unknown

(ii) MOLECULE TYPE: Genomic DNA

(iii) SEQUENCE DESCRIPTION:  SEQ ID NO: 19:

TTGGGGTGGA GGAGCTTCTG CCGTAGAAT                                     29


(2) INFORMATION FOR SEQ ID NO: 20:

(i) SEQUENCE CHARACTERISTICS:
(A) LENGTH: 31
(B) TYPE: nucleic acid
(C) STRANDEDNESS:  double
(D) TOPOLOGY:  unknown

(ii) MOLECULE TYPE: Genomic DNA

(iii) SEQUENCE DESCRIPTION:  SEQ ID NO: 20:

CGTGAGGGCC ACGGCGAGCG CGCCTAGGGG T                                  31


(2) INFORMATION FOR SEQ ID NO: 21:

(i) SEQUENCE CHARACTERISTICS:
(A) LENGTH: 34
(B) TYPE: nucleic acid
(C) STRANDEDNESS:  double
(D) TOPOLOGY:  unknown

(ii) MOLECULE TYPE: Genomic DNA

(iii) SEQUENCE DESCRIPTION:  SEQ ID NO: 21:

CTAGTCCAAG GGAAAGTATA GCCCAAGGTA CACT                               34


(2) INFORMATION FOR SEQ ID NO: 22:

(i) SEQUENCE CHARACTERISTICS:
(A) LENGTH: 32
(B) TYPE: nucleic acid
(C) STRANDEDNESS:  double
(D) TOPOLOGY:  unknown

(ii) MOLECULE TYPE: Genomic DNA

(iii) SEQUENCE DESCRIPTION:  SEQ ID NO: 22:

CTTGACGTGA AACTTGAAGA CCACCATCTC AA                                 32


(2) INFORMATION FOR SEQ ID NO: 23:

(i) SEQUENCE CHARACTERISTICS:
(A) LENGTH: 33
(B) TYPE: nucleic acid
(C) STRANDEDNESS:  double
(D) TOPOLOGY:  unknown
```

-continued (ii) MOLECULE TYPE: Genomic DNA (iii) SEQUENCE DESCRIPTION: SEQ ID NO: 23:

TTCGCGCCCA TCGTACACCG AGGCGGTATC CTC 33

(2) INFORMATION FOR SEQ ID NO: 24:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 24:

CTTGACGGAG GCGGACGGCG CTGGTACACT 30

(2) INFORMATION FOR SEQ ID NO: 25:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 25:

CTTGACACCG CAGGCCTAGA GGGCTTACCT 30

(2) INFORMATION FOR SEQ ID NO: 26:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 26:

CTTGACACCG CAGGCCTCGA GGGCTATCCT 30

(2) INFORMATION FOR SEQ ID NO: 27:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 27:

CTTGACACCG CGGGCCTCGA GGGCTATAAT 30

(2) INFORMATION FOR SEQ ID NO: 28:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 28:

-continued

CTGGACACCG CAGGCCTCGA GGGCTATCCT 30

(2) INFORMATION FOR SEQ ID NO: 29:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 29:

CTTGACACCC CAGGCCTCGA GGGGTATCCT 30

(2) INFORMATION FOR SEQ ID NO: 30:

(i) SEQUENCE CHARACTERISTICS:
(A) LENGTH: 31
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 30:

GTTTACAAAA TCCCCGCCCC CGTCCTAGCC T 31

(2) INFORMATION FOR SEQ ID NO: 31:

(i) SEQUENCE CHARACTERISTICS:
(A) LENGTH: 35
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 31:

CTTGCCAATC CGCCCCTTAG AGTGTACCAT AGCGA 35

(2) INFORMATION FOR SEQ ID NO: 32:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 32:

GTTGACCATC TTCCTCCTTG GCCTTATCCT 30

(2) INFORMATION FOR SEQ ID NO: 33:

(i) SEQUENCE CHARACTERISTICS:
(A) LENGTH: 30
(B) TYPE: nucleic acid
(C) STRANDEDNESS: double
(D) TOPOLOGY: unknown (ii) MOLECULE TYPE: Genomic DNA (iii) SEQUENCE DESCRIPTION: SEQ ID NO: 33:

GTTGACGGGA CGGGGAGGAG GGCCTATCCT 30

(2) INFORMATION FOR SEQ ID NO: 34:

-continued

```
     (i) SEQUENCE CHARACTERISTICS:
          (A) LENGTH: 30
          (B) TYPE: nucleic acid
          (C) STRANDEDNESS:  double
          (D) TOPOLOGY:  unknown

    (ii) MOLECULE TYPE: Genomic DNA

   (iii) SEQUENCE DESCRIPTION:  SEQ ID NO: 34:

CTTGTCAAGT AAGCTTAGCT ATGGTAACAT                                       30


(2) INFORMATION FOR SEQ ID NO: 35:

     (i) SEQUENCE CHARACTERISTICS:
          (A) LENGTH: 30
          (B) TYPE: nucleic acid
          (C) STRANDEDNESS:  double
          (D) TOPOLOGY:  unknown

    (ii) MOLECULE TYPE: Genomic DNA

   (iii) SEQUENCE DESCRIPTION:  SEQ ID NO: 35:

CTTGACGGGG AGGAGGCAAC GGGGTAAAAC                                       30
```

METHOD FOR AMPLIFYING AND DETECTING OF TARGET NUCLEIC ACID SEQUENCE USING THERMOSTABLE ENZYME

This is a continuation of application(s) Ser. No. 08/821,782, filed on Mar. 20, 1997, now U.S, Pat. No. 5,981,183, which is a continuation of Ser. No. 08/446,709, filed May 30, 1995 (abandoned), which is the national phase of PCT/JP94/02025 filed Dec. 1, 1993.

FIELD OF THE INVENTION

The present invention relates to a method for amplifying a specific nucleotide sequence, a method for detecting the target nucleotide sequence from RNA copy or DNA copy of the specific nucleotide sequence obtained by said method for amplification, and a kit used for said methods.

PRIOR ART

Methods for diagnosing diseases by detecting genes such as DNA and RNA have been developed to detect bacteria, viruses and the like. In certain samples, there exists sufficient amount of nucleic acids to be directly detected, however it is difficult to detect the target gene directly when the amount of the target gene is very small or when abundance ratio thereof is very small. Conventionally, the target gene is increased by culturing cells or bacteria. However, there has been a defect that these methods require a long time.

Polymerase chain reaction (PCR; JP-B 4-67957) is also known as another method for amplifying the target gene. In this method, the degree of amplification of the target gene is adjusted by a number of the cycle. Theoretically, the amplification factor is calculated to be $2_n$ (n is a number of the cycle). Twenty-five to thirty cycles have been required to amplify the target gene to a level where it can be detected effectively.

In addition, amplification systems based on replicated RNA are known as a further method for amplifying nucleic acids (JP-A 2-5864, JP-A 2-500565 and JP-A 2-501532). In these methods, using a primer containing a promoter sequence of DNA dependent RNA polymerase, a double stranded DNA is synthesized from the target nucleic acid, and the RNA corresponding to the target nucleic acid is synthesized by DNA dependent RNA polymerase using the double stranded DNA synthesized as a template. Then, a DNA/RNA chain is synthesized from the RNA which is synthesized by RNA dependent DNA polymerase, and the DNA/RNA chain is separated to obtain a single stranded DNA. As methods for separation to DNA, a heat-denaturation (JP-A 2-500565 and JP-A 2-501532) and a method using ribonuclease H (JP-A 2-5864) are known. Using the single stranded DNA thus obtained and a primer, a double stranded DNA containing a promoter sequence of DNA dependent RNA polymerase is synthesized, and transcription to RNA is carried out. According to this method, dozens to thousands of RNA molecules can be transcribed and amplified from a molecule of the double stranded nucleic acid by DNA dependent RNA polymerase, so that the amplification efficiency per cycle is higher than PCR method. When ribonuclease H is used, a thermal cycling which has been required in PCR method is not required, so that amplification can be carried out more easily.

PROBLEMS TO BE SOLVED BY THE INVENTION

Amplification efficiency is high in the amplification system based on replicated RNA. However, because of a poor heat stability of conventional enzymes, namely RNA dependent DNA polymerase, DNA dependent RNA polymerase and DNA dependent DNA polymerase, the reaction temperature does not have to be high, and non-specific hybridization between the nucleic acid as a template and the primer cannot be avoidable, so that decrease of the specificity is a problem. In addition, the instability of the enzymes creates a severe problem in supplying and storing enzymes, and storage in a frozen state or in a refrigerator is required.

Moreover, heat is used to denature a double stranded nucleic acid in a method for amplification without using ribonuclease H. In this method, it is necessary to add the enzymes sequentially every time heating is carried out because of instability of the enzymes.

The object of the invention is to solve the problems that the specificity is decreased by non-specific hybridization, and that the enzymes are unstable in supply and storage.

MEANS TO SOLVE THE PROBLEMS

Figure 1:
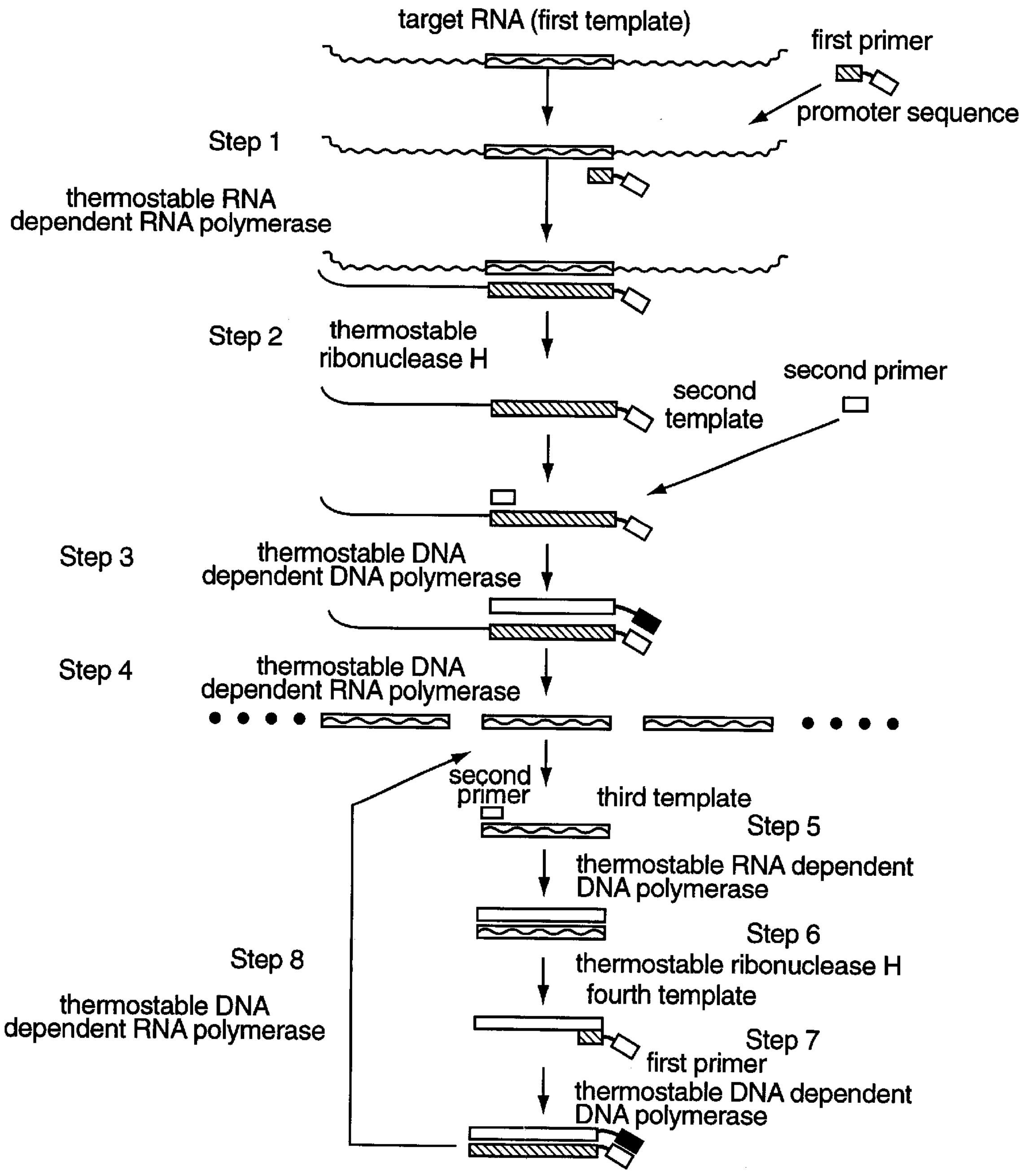
FIG. 1 shows a process of the amplification method of the present invention in case that the target nucleic acid is RNA.

One aspect of the present invention is a method for amplifying the target nucleic acid sequence using thermostable enzymes, in which the copy number of the target nucleic acid sequence is increased in a reaction medium at a substantially constant temperature, that comprises following steps:

Step 1: hybridizing the first primer containing a sequence sufficiently complementary to the nucleic acid sequence (RNA) of the first template, and a promoter sequence at 5'-terminal side thereof, with the first template RNA of single strand which is the target nucleic acid optionally treated by denaturation, and elongating the first primer by thermostable RNA dependent DNA polymerase to obtain the first primer elongation product (DNA) which is the second template complementary to the first template RNA;

Step 2: separating the second template DNA from the first template RNA to obtain the second template nucleic acid of single strand (DNA) by a thermostable ribonuclease H which degrades only RNA of a RNA/DNA hybrid;

Step 3: hybridizing the second primer containing a nucleic acid sequence complementary to the second nucleic acid sequence (DNA) with the second template DNA of single strand, and elongating the second primer by thermostable DNA dependent DNA polymerase to obtain the second primer elongation product (DNA) complementary to the second template DNA (in such a way, a double stranded DNA intermediate containing a promoter sequence which can operate is produced in the upstream of the target nucleic acid sequence);

(wherein, nucleic acid sequence of the first primer or the second primer is sufficiently complementary or homologous to the target nucleic acid sequence, and the 3'-terminal of the first primer is directed to the 3'-terminal of the second primer on the complementary chain.)

Step 4: producing the third template RNA containing a sequence complementary to said target nucleic acid sequence (the first template RNA) from said double stranded DNA. intermediate, using thermostable DNA dependent RNA polymerase which can recognize said promoter sequence;

Step 5: hybridizing said second primer with the third template RNA of single strand, and elongating said second primer by thermostable RNA dependent DNA polymerase to obtain the second primer elongation product (DNA) which is a fourth template complementary to the third template RNA;

Step 6: separating the fourth template DNA from the third template RNA to obtain the fourth template nucleic acid (DNA) of single strand by thermostable ribonuclease H which degrades only RNA of a RNA/DNA hybrid;

step 7: hybridizing said first primer with the fourth template DNA of single strand, and carrying out elongation by thermostable DNA dependent DNA polymerase to obtain the first primer elongation product (DNA) complementary to the fourth template DNA, and the fourth template DNA elongation product complementary to the promoter sequence of said first primer (in such a way, a double stranded DNA intermediate containing a promoter sequence which can operate is produced in the upstream of the target nucleic acid sequence);

(wherein, nucleic acid sequence of the first primer or the second primer is sufficiently complementary or homologous to the target nucleic acid sequence, and the 3'-terminal of the first primer is directed to the 3'-terminal of the second primer on the complementary chain)

Step 8: increasing copy number of the third template RNA of single strand containing a sequence complementary to said target nucleic acid sequence (the first template RNA) from said double stranded DNA intermediate, using thermostable DNA dependent RNA polymerase which can recognize said promoter sequence; and Step 9: optionally repeating said Step 5 to Step 8 as many times as required using said RNA copy.

Another aspect of the present invention is a method for amplifying the target nucleic acid sequence using thermostable enzymes, in which the copy number of the target nucleic acid sequence is increased in a reaction medium, that comprises following steps:

Step 1: hybridizing the first primer containing a sequence sufficiently complementary to the nucleic acid sequence of the first template, and a promoter sequence at 5'-terminal side thereof, with the first template DNA of single strand which is the target nucleic acid optionally treated by denaturation, and elongating the first primer by thermostable DNA dependent DNA polymerase to obtain the first primer elongation product (DNA) which is the second template complementary to the first template DNA;

Step 2; separating the second template DNA from the first template DNA to obtain the second template nucleic acid of single strand (DNA);

Step 3: hybridizing the second primer containing a nucleic acid sequence (DNA) complementary to the second nucleic acid sequence (DNA) with the second template DNA of single strand, and elongating the second primer by thermostable DNA dependent DNA polymerase to obtain the second primer elongation product (DNA) complementary to the second template DNA (in such a way, a double stranded DNA intermediate containing a promoter sequence which can operate is produced in the upstream of the target nucleic acid sequence);

(wherein, nucleic acid sequence of the first primer or the second primer is sufficiently complementary or homologous to the target nucleic acid sequence, and the 3'-terminal of the first primer is directed to the 3'-terminal of the second primer on the complementary chain.);

Step 4: producing the third template RNA containing a sequence complementary to said target nucleic acid sequence (the first template DNA) from said double stranded DNA intermediate, using thermostable DNA dependent RNA polymerase which can recognize said promoter sequence;

Step 5: hybridizing said second primer with the third template RNA of single strand, and elongating said second primer by thermostable RNA dependent DNA polymerase to obtain the second primer elongation product (DNA) which is a fourth template complementary to the third template RNA;

Step 6: separating the fourth template DNA from the third template RNA to obtain the fourth template nucleic acid (DNA) of single strand by thermostable ribonuclease H which degrades only RNA of RNA/DNA hybrid;

Step 7: hybridizing the first primer with the fourth template DNA of single strand, and carrying out elongation by thermostable DNA dependent DNA polymerase to obtain the first primer elongation product (DNA) complementary to the fourth template DNA, and the fourth template DNA elongation product complementary to the promoter sequence of said first primer (in such a way, a double stranded DNA intermediate containing a promoter sequence which can operate is produced in the upstream of the target nucleic acid sequence);

(wherein, nucleic acid sequence of the first primer or the second primer is sufficiently complementary or homologous to the target nucleic acid sequence, and the 3'-terminal of the first primer is directed to the 3'-terminal of the second primer on the complementary chain)

Step 8: increasing copy number of the third template RNA of single strand containing a sequence complementary to said target nucleic acid sequence from said double stranded DNA intermediate, using thermostable DNA dependent RNA polymerase which can recognize said promoter sequence; and Step 9: optionally repeating said Step 5 to Step 8 as many times as required using said RNA copy.

Another aspect of the present invention is a method for detecting the target nucleic acid sequence, which comprises hybridizing a labelled probe with the single stranded RNA, the double stranded DNA, or the DNA/RNA hybrid which is a product by amplification methods above described after optional denaturation treatment, and detecting the label of the labelled probe hybridized or the label of the labelled probe not hybridized.

Further aspect of the present invention is a kit for amplifying a specific nucleic acid sequence. One aspect of such a kit is the kit for amplifying a specific nucleic acid sequence, which comprises (a) the first primer containing a sequence sufficiently complementary to the nucleic acid sequence of the first template, and a promoter sequence at 5'-terminal side thereof, (b) the second primer containing a nucleic acid sequence complementary to the nucleic acid sequence of the second template, (c) thermostable ribonuclease H, (d) thermostable RNA dependent DNA polymerase, (e) thermostable DNA dependent RNA polymerase, (f) thermostable DNA dependent DNA polymerase, (g) ribonucleoside triphosphates, and (h) deoxyribonucleoside triphosphates, provided that nucleic acid sequence of the first primer or the second primer is sufficiently complementary or homologous to the target nucleic acid sequence, and the 3'-terminal of the first primer is directed to the 3'-terminal of the second primer on the complementary chain.

Another aspect of said kit is the kit for amplifying a specific nucleic acid sequence, which comprises (a) the first primer containing a sequence sufficiently complementary to the nucleic acid sequence of the first template, and a promotor sequence at 5'-terminal side thereof, (b) the second primer containing a nucleic acid sequence complementary to the nucleic acid sequence of the second template, (c) thermostable ribonuclease H, (d) thermostable DNA dependent RNA polymerase, (e) thermostable DNA dependent DNA polymerase having a RNA dependent DNA polymerase activity, (f) ribonucleoside triphosphates, and (g) deoxyribonucleoside triphosphates, provided that nucleic acid sequence of the first primer or the second primer is sufficiently complementary or homologous to the target nucleic acid sequence, and the 3'-terminal of the first primer is directed to the 3'-terminal of the second primer on the complementary chain.

Further aspect of the kit is the kit for amplifying a specific nucleic acid sequence, which comprises (a) the first primer containing a sequence sufficiently complementary to the nucleic acid sequence of the first template, and a promotor sequence at 5'-terminal side thereof, (b) the second primer containing a nucleic acid sequence complementary to the nucleic acid sequence of the second template, (c) thermostable DNA dependent RNA polymerase, (d) thermostable DNA dependent DNA polymerase having, a RNA dependent DNA polymerase activity and a ribonuclease H activity, (e) ribonucleoside triphosphaces, and (f) deoxyribonucleoside triphosphates, provided that nucleic acid sequence of the first primer or the second primer is sufficiently complementary or homologous to the target nucleic acid sequence, and the 3'-terminal of the first primer is directed to the 3'-terminal of the second primer on the complementary chain.

Another aspect of said kit is the kit for amplifying a specific nucleic acid sequence, which comprises (a) the first primer containing a sequence sufficiently complementary to the nucleic acid sequence of the first template, and a promotor sequence at 5'-terminal side thereof, (b) the second primer containing a nucleic acid sequence complementary to the nucleic acid sequence of the second template, and a promoter sequence at 5'-terminal side thereof, (c) thermostable ribonuclease H, (d) thermostable RNA dependent DNA polymerase, (d) thermostable DNA dependent RNA polymerase, (f) thermostable DNA dependent DNA polymerase, (g) ribonucleoside triphosphates, and (h) deoxyribonucleoside triphosphates, provided that nucleic acid sequence of the first primer or the second primer is sufficiently complementary or homologous to the target nucleic acid sequence, and the 3'-terminal of the first primer is directed to the 3'-terminal of the second primer on the complementary chain.

Another aspect of said kit is the kit for amplifying a specific nucleic acid sequence, which comprises (a) the first primer containing a sequence sufficiently complementary to the nucleic acid sequence of the first template, and a promotor sequence at 5'-terminal side thereof, (b) the second primer containing a nucleic acid sequence complementary to the nucleic acid sequence of the second template, and a promoter, sequence at 5'-terminal side thereof, (c) thermostable ribonuclease H, (d) thermostable DNA dependent RNA polymerase, (e) thermostable DNA dependent DNA polymerase having a RNA dependent DNA polymerase activity, (f) ribonucleoside triphosphates, and (g) deoxyribonucleoside triphosphates, provided that nucleic acid sequence of the first primer or the second primer is sufficiently complementary or homologous to the target nucleic acid sequence, and the 3'-terminal of the first primer is directed to the 3'-terminal of the second primer on the complementary chain.

Another aspect of the kit of the present invention is the kit for amplifying a specific nucleic acid sequence, which comprises (a) the first primer containing a sequence sufficiently complementary to the nucleic acid sequence of the first template, and a promotor sequence at 5'-terminal side thereof, (b) the second primer containing a nucleic acid sequence complementary to the nucleic acid sequence of the second template, and a promoter sequence at 5'-terminal side thereof, (c) thermostable DNA dependent RNA polymerase, (d) thermostable DNA dependent DNA polymerase having a RNA dependent DNA polymerase activity and a ribonuclease H activity, (e) ribonucleoside triphosphates, and (f) deoxyribonucleoside triphoshates, provided that nucleic acid sequence of the first primer or the second primer is sufficiently complementary or homologous to the target nucleic acid sequence, and the 3'-terminal of the first primer is directed to the 3'-terminal of the second primer on the complementary chain.

The target nucleic acid can be either DNA or RNA. When the target nucleic acid is double stranded or it taker a higher-order structure though it is single stranded, the target nucleic acid is made into a single strand by a treatment such as preliminary heating, or acid or alkali treatment, then subjected to the amplification reaction. In addition, when the target nucleic acid is DNA, the amplification method of the present invention can be carried out after the target nucleic acid is transformed into RNA by a know conventional method.

The first primer used in the present invention contains a nucleic acid sequence sufficiently complementary to the nucleic acid sequence of the first template which is the target nucleic acid sequence, and a promoter sequence at 5'-terminal side thereof. The 3'-terminal is directed to the 3'-terminal of the second primer on the complementary chain.

Also, the second primer contains a nucleic acid sequence sufficiently complementary to the nucleic acid sequence of the second template, and sufficiently homologous to the target nucleic acid sequence.

The second primer can optionally contain a promoter sequence at 5'-terminal side thereof in addition to a nucleic acid sequence complementary to the nucleic acid sequence of the second template. When the second primer contains a promoter sequence, the promoter sequences of the first primer and the second primer can be same or different. When they are different, several thermostable DNA dependent RNA polymerases which act individual promoters are optionally used.

According to the nature of the promoter, a thermostable DNA dependent RNA polymerase can be selected to act on both promoters. The amplification efficiency can be further elevated by conferring promoter functions on both the first and the second primers.

Design of the promoters is varied according to the target nucleic acid to be amplified. When amplification is carried out in a highly specific condition, it is desirable that Tm of the primers are 50–70° C. When amplification is carried out at a temperature below this Tm, it is necessary that sequences of the primers are sufficiently examined to maintain the specificity, and it is difficult to select the nucleic acid sequences to be amplified randomly.

The promoter sequences used in the present invention are not limited, however it is necessary that the sequences operate in such a mode that thermostable DNA dependent RNA. polymerase can act on them. For example, the following promoter sequences that can be acted on by a DNA dependent RNA polymerase from *Thermus thermophilus,*

5'-CTTGACAAAAAGGAGGGGGATTGATTGATAGCAT [SEQ ID NO:6]-3'

5'-TTCGCGCCCATCGTACACCGAGGCGGTATCCTC [SEQ ID NO:7]-3'

5'-CTTGACGGAGGCGGACGGCGCTGGTACACT[SEQ ID NO:8]-3'

5'-CTGGACAGGGCCCCCGTGTCCCGCTATCCT[SEQ ID NO:9]-3'

5'-CTAGCCTCAGGGCTTCCATGGGTGCTATACT[SEQ ID NO:10]-3'

5'-CTTGACCCCGCAGGCCTCGAGGGCTTACCT[SEQ ID NO:11]-3'are known.

Generally, a promoter sequence is followed by a spacer sequence that extends to the replication origin. For example, GGCTTT which follows CTTGACAAAAAGGAGGGGGATTGATAGCAT[SEQ ID NO:12] is known. The spacer sequence before the replication origin, or the spacer sequence with the sequence containing the region that initiates replication, is regarded as the promoter. In fact, it is also known that efficiency of transcription and replication is higher when the promoter containing this sequence is used. Therefore, a primer with a promoter which contain this sequence of the sequence can be designed to increase efficiency of transcription and amplification. In the present, invention, even a primer, to which a sequence containing a spacer sequence extending to the replication origin is linked, can be amplified.

As promoter sequences, the following sequences are exemplified.

5'-CTTGACGCCGCCCAGGGCGGGCCTCTACCCT [SEQ ID NO:13]-3'

5'-TTTGAGGGCCTGGGGCAGTACCTCTTCT[SEQ ID NO:14]-3'

5'-TTTGTAAAGTGCTTTATTTCACAAAACT[SEQ ID NO:15]-3'

5'-TTTCACAAAACTGTCCCTCCCCCCGGGTTAGACT [SEQ ID NO:16]-3'

5'-TTGACACTCTCGGGCGGGTGTGCTAGCCT[SEQ ID NO:17]-3'

5'-CTTGAGGATCTCGGGGAGGCGGGCTTCCAT[SEQ ID NO:18]-3'

5'-TTGGGGTGGAGGAGCTTCTGCCGTAGAAT[SEQ ID NO:19]-3'

5'-CTTGACAAAAAGGAGGGGGATTGATAGCAT[SEQ ID NO:12]-3'

5'-CGTGAGGGCCACGGCGAGCGCGCCTAGGGGT [SEQ ID NO:20]-3'

5'-CTAGTCCAAGGGAAAGTATAGCCCAAGGTACACT [SEQ ID NO:21]-3'

5'-CTTGACGTGAAACTTGAAGACCACCATCTCAA [SEQ ID NO:22]-3'

5'-TTCGCGCCCATCGTACACCGAGGCGGTATCCTC [SEQ ID NO:23]-3'

5'-CTTGACGGAGGCGGACGGCGCTGGTACACT[SEQ ID NO:24]-3'

5'-CTGGACAGGGCCCCCGTGTCCCGCTATCCT[SEQ ID NO:9]-3'

5'-CTAGCCTCAGGGCTTCCATGGGTGCTATACT[SEQ ID NO:10]-3'

5'-CTTGACCCCGCAGGCCTCGAGGGCTTACCT[SEQ ID NO:11]-3'

5'-CTTGACACCGCAGGCCTAGAGGGCTTACCT[SEQ ID NO:25]-3'

5'-CTTGACACCGCAGGCCTCGAGGGCTATCCT[SEQ ID NO:26]-3'

5'-CTTGACACCGCGGGCCTCGAGGGCTATAAT[SEQ ID NO:27]-3'

5'-CTGGACACCGCAGGCCTCGAGGGCTATCCT[SEQ ID NO:28]-3'

5'-CTTGACACCCCAGGCCTCGAGGGGTATCCT[SEQ ID NO:29]-3'

5'-GTTTACAAAATCCCCGCCCCCGTCCTAGCCT[SEQ ID NO:30]-3'

5'-CTTGCCAATCCGCCCCTTAGAGTGTACCATAGCG A[SEQ ID NO:31]-3'

5'-GTTGACCATCTTCCTCCTTGGCCTTATCCT[SEQ ID NO:32]-3'

5'-GTTGACGGGACGGGGAGGAGGGCCTATCCT[SEQ ID NO:33]-3'

5'-CTTGTCAACTAACCTTACCTATGGTAACAT[SEQ ID NO:34]-3'

5'-CTTGACGGGGAGGAGGCAACGGGGTAAAAC [SEQ ID NO:35]-3'

Generally, promoters of phages have high specificities, however, promoters of other organisms do not always have high specificities. A term herein used "high specificity" means that the amount of the promoter sequences, on which DNA. dependent RNA polymerase depending on the promoters can act, is very small though one or more kinds of the promoter sequences of the DNA dependent RNA polymerase exist, or that the sequence has a very low activity as a promoter. Therefore, the term means that the DNA dependent RNA polymerase depending on the promoters can act substantially without problems while various promoters exist in the sample nucleic acid to be detected.

On the other hand, in bacteria and the other organisms, the promoter sequences on which DNA dependent RNA polymerase acts is not always only of one kind, and the existence of one or more kinds of promoter sequences is known. Sequences sharing a common sequence to a high extent exist in bacteria and fungi. Therefore, the promoter sequences, on which the DNA dependent RNA polymerase act, can exist also in the sample nucleic acid to be detected.

In the present invention, investigation has been carried out, considering such points, so that amplification and detection with a high specificity can be performed by reacting at 50–70° C. where thermostable DNA dependent RNA polymerase can act because the non-specific promoter function is not expressed. A term herein used "the double stranded DNA intermediate containing a promoter sequence which can operate in the upstream of the target nucleic acid sequence" means the double stranded DNA intermediate in Step 3 or Step 4 (FIG. 1 or FIG. 2 ), and that the intermediate has a function to initiate the RNA synthesis using DNA as template by the action of thermostable DNA dependent RNA polymerase. RNA produced by the function of said promoter has a sequence complementary to the target RNA.

A term herein used "a thermostable enzyme" means an enzyme which can act at 50–70° C., and is slightly denatured even under the condition of 90–95° C., 10 sec-10 min, where heat denaturation of nucleic acids is carried out. In addition, generally, such an enzyme generally is sufficiently stable with storage in a refrigerator or at room temperature, and, in many cases, preservation in a frozen state is not necessary.

As for thermostable RNA dependent DNA polymerase (also referred as thermostable reverse transcriptase), it is known that the activity exists in DNA dependent DNA polymerase from *Thermus thermophilus* and *Thermus aquaticus.*

As thermostable DNA dependent RNA polymerase (also referred as thermostable RNA polymerase), the enzyme from *Thermus thermophilus* is exemplified. Said thermostable DNA dependent RNA polymerase can recognize a promoter sequence.

As thermostable DNA dependent DNA polymerase (also referred as thermostable DNA polymerase), the enzymes from *Thermus thermophilus, Thermus aquaticus, Pyrococcus furiosis, Thermococcus litoralis* and *Thermus flavus* are exemplified.

As thermostable ribonuclease H, the enzyme from *Thermus thermophilus* is exemplified, however other enzymes which fit the thermostability of the present invention can be used.

Generally, it is known that a DNA dependent EDNA polymerase activity exists in RNA dependent DNA polymerase, and that a RNA dependent DNA polymerase activity exists in DNA dependent DNA polymerase from *Thermus thermophilus* and *thermus aquaticus.* A DNA polymerase having both activities can be used commonly.

In addition, the inventors found that thermostable DNA dependent DNA polymerase has a thermostable ribonuclease H activity (Japanese patent application 6-258190). Therefore, by using thermostable DNA-dependent DNA polymerase from *Thermus thermophilus,* three enzyme activities are available for use, as compared, for instance, to the use of thermostable RNA-dependent DNA polymerase and thermostable ribonuclease H.

As for a thermostable enzyme used in the present invention, it is preferable that thermostable RNA dependent DNA polymerase, thermostable ribonuclease H and thermostable DNA dependent DNA polymerase are an enzyme.

As such an enzyme, the enzyme from *Thermus thermophilus* which has the following physical and chemical properties is preferred:

(1) catalyzing the following reactions:
  (i) synthesizing DNA using RNA as a template.
  (ii) producing a single stranded DNA by the specific and endo mode action on only RNA of d double stranded RNA/DNA.
  (iii) synthesizing DNA using DNA as a template.
(2) molecular weight: 85,000–95,000
(3) heat stability: retaining more than 50% of the original activity after treatment at 75° C. for 2 hours.
(4) optimum pH: about 7.5–9.3

Production of said enzyme is described in Japanese patent application 6-258190.

That is, said enzyme can be obtained by culturing a thermophilic bacterium *Thermus thermophilus* HB8 (ATCC 27634), and collecting the thermostable ribonuclease H having physical and chemical properties above mentioned from the culture.

In Step 1 of the method of the present invention, the first primer is hybridized with the first template nucleic acid of single strand optionally treated by denaturation, and the primer is elongated by thermostable RNA dependent DNA polymerase and/or thermostable DNA dependent DNA polymerase in the presence of deoxyribonucleoside triphosphates to obtain the first primer elongation product which is the second template complementary to the first template nucleic acid.

When the first template is RNA, the first primer is elongated by thormostable RNA dependent DNA polymerase to obtain an elongated DNA product. When the first template is DNA, the first primer is elongated by thermostable DNA dependent DNA polymerase to obtain an elongated DNA product. When the target nucleic acid sequence contains DNA and RNA, the first primer is elongated by thermostable DNA dependent DNA polymerase and thermostable RNA dependent DNA polymerase to obtain an elongated DNA product (Step 1 of FIG. 1 and FIG. 2).

When the first template is RNA, Steps 2–9 is carried out as follows (FIG. 1).

In Step 2, the second template DNA is separated from the first template RNA by thermostable ribonuclease H which degrades specifically only RNA of a RNA/DNA hybrid to obtain the second template nucleic acid of single strand (DNA).

In Step 3, the second primer containing a nucleic acid sequence complementary to the second template nucleic acid sequence (DNA) is hybridized with the second template DNA of single strand, and the second primer is elongated by thermostable DNA dependent DNA polymerase to obtain the second primer elongation product (DNA). In such a way, a double stranded DNA intermediate containing the target nucleic acid sequence linked to a promoter sequence which can operate in the upstream of the target nucleic acid sequence is produced. Nucleic acid sequence of the first primer or the second primer is sufficiently complementary or homologous to the target nucleic acid sequence, and the 3'-terminal of the first primer is directed to the 3'-terminal of the second primer on the complementary chain.

In Step 4, the third template RNA of single strand containing a sequence complementary to said target nucleic acid sequence (the first template RNA) is produced from said double stranded DNA intermediate, using thermostable DNA dependent RNA polymerase which can recognize said promoter sequence.

In Step 5, said second primer is hybridized with the third template RNA of single strand, and the third primer is elongated by thermostable RNA dependent DNA polymerase to obtain the second primer elongated (DNA) which is the fourth template complementary to the third template RNA.

In Step 6, the fourth template DNA is separated from the third template RNA by thermostable ribonuclease H which degrades specifically only RNA of a RNA/DNA hybrid to obtain the fourth template nucleic acid of single strand (DNA).

In Step 7, said first primer is hybridized with the fourth template DNA of single strand, and elongation is carried out by thermostable DNA dependent DNA polymerase to obtain the first primer elongated (DNA) complementary to the fourth template DNA, and the fourth template DNA elongated complementary to a promoter sequence of said primer. In such a way, a double stranded DNA intermediate containing the target nucleic acid sequence linked to a promoter sequence which can operate in the upstream, is produced. Nucleic acid sequence of the first primer or the second primer is sufficiently complementary or homologous to the target nucleic acid sequence, and the 3'-terminal of the first primer is directed to the 3'-terminal of the second primer on the complementary chain.

In Step 8, the copy of the third template RNA of single strand containing a sequence complementary to said target nucleic acid sequence (the first template RNA) is increased from said double stranded DNA intermediate, using thermostable DNA dependent ANA polymerase which can recognize said promoter sequence.

Then, in Step 9, optionally repeating said Step 5 to Step 8 as many times as required using said RNA copy.

Figure 2:
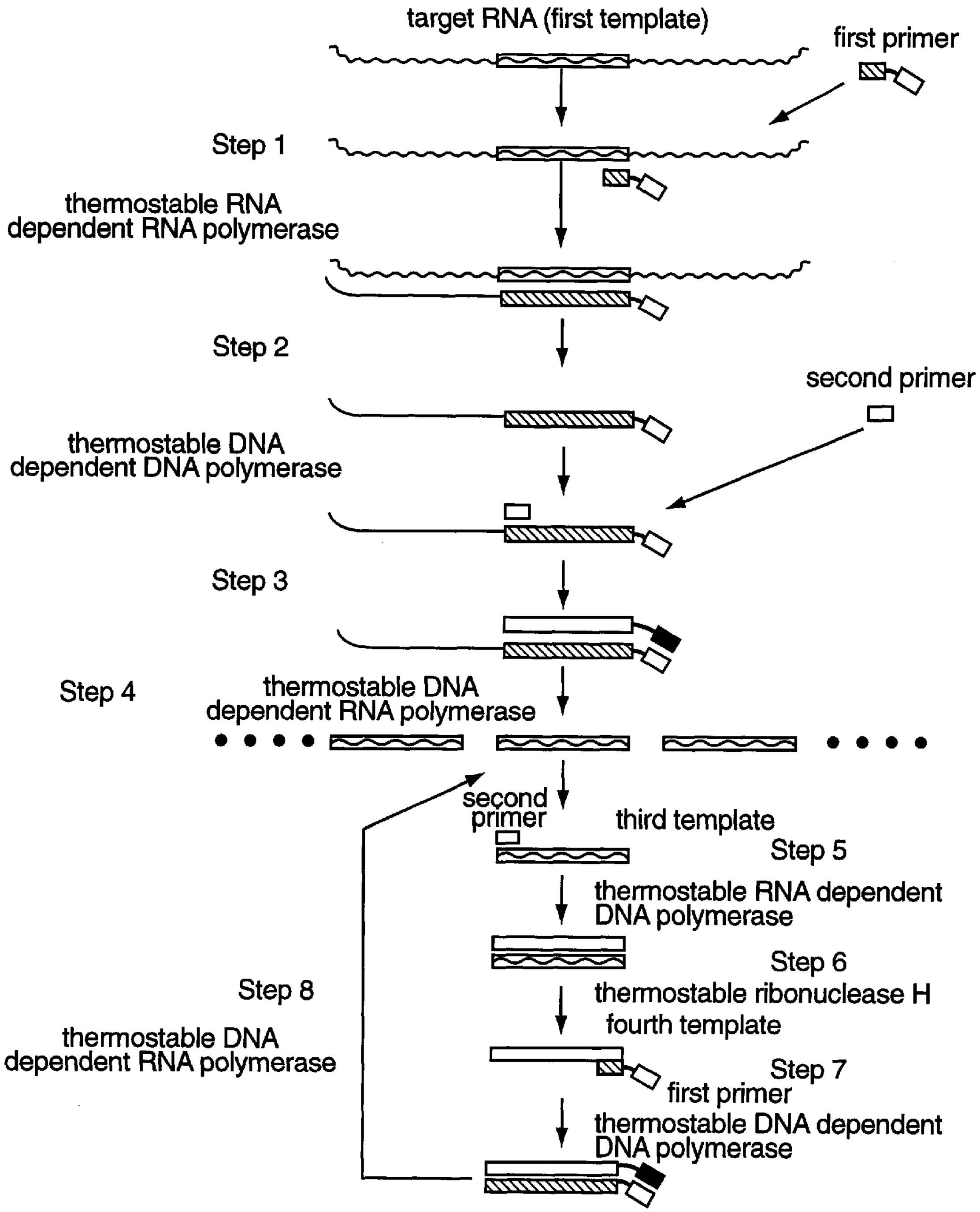
FIG. 2 shows a process of the amplification method of the present invention in case that the target nucleic acid is DNA.

When the first template is DNA, Steps 2–9 are carried out as follows (FIG. 2).

In Step 2, the second template DNA is separated from the first template DNA to obtain the second nucleic acid of single strand (DNA).

In Step 3, the second primer containing a nucleic acid sequence (DNA) complementary to the second template nucleic acid sequence (DNA) is hybridized with the second template DNA of single strand, and the second primer is elongated by thermostable DNA dependent DNA polymerase to obtain the second primer elongating product (DNA). In such a way, a double stranded DNA intermediate containing EL promoter sequence which can operate is produced in the upstream of the target nucleic acid sequence. Nucleic acid sequence of the first primer or the second primer is sufficiently complementary or similar to the target nucleic acid sequence, and the 3'-terminal of the first primer is directed to the 3'-terminal of the second primer on the complementary chain.

In Step 4, the copy number of the third template RNA of single strand containing a sequence complementary to said target nucleic acid sequence (the first template) is increased from said double stranded DNA intermediate, using thermostable DNA dependent RNA polymerase which can recognize said promoter sequence.

In Step 5, said second primer is hybridized with the third template RNA of single strand, and the second primer is elongated by thermostable RNA dependent DNA polymerase to obtain the second primer elongated (DNA) which is the fourth template complementary to the third template RNA.

In Step 6, the fourth template DNA is separated from the third template RNA by thermostable ribonuclease H which degrades specifically only RNA of a RNA/DNA hybrid to obtain the fourth template nucleic acid of single strand (DNA).

In Step 7, the first primer is hybridized with the fourth template DNA of single strand, and elongation is carried out by thermostable DNA dependent DNA polymerase to obtain the fourth template DNA elongated complementary to the fourth template DNA. In such a way, a double stranded DNA intermediate containing the target nucleic acid sequence linked to a promoter sequence which can operate in the upstream, is produced. Nucleic acid sequence of the first. primer or the second primer is sufficiently complementary or homologous to the target nucleic acid sequence, and the 3'-terminal of the first primer is directed to the 3'-terminal of the second primer on the complementary chain.

In Step 8, the copy of the third template RNA of single strand containing a sequence complementary to said target nucleic acid sequence (the first template) is increased from said double stranded DNA intermediate, using thermostable DNA dependent RNA polymerase which can recognize said promoter sequence.

Then, in Step 9, optionally repeating said Step 5 to Step 8 as many times as required using said RNA copy.

When a group consisting of plural thermostable enzymes is used in the method of the present invention, these enzymes do not lose their activities in heat denaturation treatment, so that it is not necessary to add enzymes sequentially. In the conventional method for amplifying nucleic acid, normal enzymes act at a room temperature, however these enzymes cannot be used at a high temperature because they are unstable. On the other hand, to maintain the specificity of the primer, it is desirable that the reaction temperature is high. Therefore, to maintain the specificity of the primer at a lower temperature, it is necessary to limit the primer sequence to a large extent and also to enhance stringency at a low temperature by adding an organic solvent, such as dimethylformamide. This is not preferable.

Oligonucleotides which are the first primer and the second primer can be synthesized by phosphoamidite method using for example a DNA synthesizer model 391 (manufactured by Applied Biosystems Inc. (ABI)). As other methods of synthesis, phosphotriester method, H-phosphonate method, and thiophosphite method are exemplified. The oligonucleotide can be isolated from biological sources, for example a digest with restriction endonuclease. The length and structure are not limited when the nucleic acid is designed to operate as a primer.

Generally, length of a primer is 6–50 nucleotides, preferably 10–30 nucleotiudes. A spacer can be inserted between the promoter region and the promoter sequence. The length of the spacer is 0–100 nucleotides, preferably 0–20 nucleotides.

Concentrations of the first primer and the second primer are generally 10–50000 nM, preferably 100–500 nM. Concentrations of ribonucleoside triphosphate and deoxyribonucleoside triphosphate are generally 10–10000 μM (dNTP) and 10–10000 μM (rNTP), preferably 100–2000 μM (dNTP) and 100–4000 μM (rNTP). The concentration ratio of ribonucleoside triphosphate to deoxyribonucleoside triphosphate is generally 1/10–2/1, preferably 1/2–3/4.

As for thermostable RNA dependent DNA polymerase, it is known that thermostable DNA dependent RNA polymerases from *Thermus thermophilus* and *Thermus aquaticus* have this activity. It is known that the DNA polymerase activity dependent on RNA is expressed by selecting the nature and amount of the divalent metal ion. However, it is not easy to express both RNA dependent DNA polymerase activity and DNA dependent DNA polymerase activity. The inventors have investigated the condition where both activities can be expressed to fullest extent, and have found that the condition where the ratio of Mg ion to Mn ion is 1:1, preferably 1.5:1–3:1 is desirable. In addition, the nature and amount of divalent metal ion is important to DNA dependent RNA polymerase. To express these three activities to fullest extent, the condition where the ratio of Mg ion to Mn ion is 1:1–4:1, preferably 1.5:1–3:1, and dNTP:rNTP is 1:10–10:1, preferably 1:2–3.5 is desirable.

Thermostable enzymes are known in the art, however the use of the combination of the plural thermostable enzymes of the present invention has not previously been disclosed. In addition, the amplification reaction of nucleic acids does not occur by simply combining thermostable enzymes, and a high efficiency of amplification cannot be attained easily using the cycle reaction.

In the present invention, the reaction time is varied by conditions such as the nucleic acid sequence to be amplified, the sequence and Tm of the primer, and the amount of the enzyme. The suitable reaction time per cycle is about 5–300 min, preferably 20–120 min. There is the concept of what is called cycle, however the number of cycle is not shown because the reaction is carried out at a substantially constant temperature. These conditions are dictated by the efficiency of amplification, the amount of amplification, and the time required. In many cases, the target nucleic acid has a high-order structure though it is single stranded, therefore the temperature of the reaction mixture can be elevated to 90–95° C. at the beginning of the reaction. In this case, heating can be performed after preparation of the reaction mixture because the enzyme does not degrade substantially. Thus, the method is excellent also from viewpoint of convenience and prevention of contamination. Amplification can be carried out only by maintain the reaction mixture at a constant temperature of 50–70° C. during the reaction. The amplification can be carried out easily because it requires no particular apparatus.

The nucleic acid amplified by the method of the invention can be detected if desired. The detection can be carried out by measuring RNA copy, by measuring the double stranded DNA containing a promoter sequence, or by measuring DNA/RNA hybrid. These detections can be done by common methods for measurement. In the elongation reaction by nucleic acid polymerase, and the transcription reaction, labelled compounds such as $^{32}P$ or biotin labelled nucleotides are used as riboxynucleoside triphosphates or deoxyribonucleoside triphosphates to be added, the label is incorporated into the amplified product, then the amount of the label is measured. In addition, a method in which the label in the amplified product is measured using a labelled primer, and a method in which the amplified nucleic acid is detected using a labelled probe, are exemplified. As practical methods for detection, fractionation by electrophoresis, southern blotting, northern blotting, dot blotting, slot blotting, sandwich hybridization are exemplified. The concentration of the nucleic acid in the sample to be tested can be determined by a quantitative measurement. In addition, the quantitativeness can be elevated by a method using an inner standard (JP-A 62-205800)

In methods for detection using a labelled primer or a labelled probe, known labelled materials such as radioisotopes, enzymes, fluorescent materials and luminescent materials can be used as labelled materials. Also, reagents used in the present invention can be each kit above described according to a known method. Forms, concentrations, and so on of the reagents themselves are not limited otherwise mentioned.

Thus, according to the present invention, the amplification reaction of the target nucleic acid can be performed at a sufficiently high temperature to avoid non-specific hybridization between the nucleic acid template and the primer, by using RNA dependent DNA polymerase, DNA dependent DNA polymerase, DNA dependent RNA polymerase and ribonuclease H required in the amplification system based on replicated RNA, all of which are thermostable.

Consequently, non-specific amplification does not occur, and the amplification with a high specificity can be performed. Also, thermostable enzymes are stable at room temperature as well as at a low temperature. Their activities hardly decrease in supply and preservation, so that it is possible to solve a problem of instability. In addition, even when denaturation is carried out by heating instead of ribonuclease H, deactivation of the enzymes is prevented, and amplification can be carried out without sequential addition of enzymes by using thermostable enzymes.

The present invention is further described in detail below by showing reference examples, examples and comparative examples. In examples, RNA dependent DNA polymerase is referred as reverse transcriptase, DNA dependent DNA polymerase as DNA polymerase, ribonuclease H as RNase H, and DNA dependent RNA polymerase as RNA polymerase.

Reference Example 1

Synthesis of Various Oligonucleotides

Using a DNA synthesizer model 391 (manufactured by ABI), various oligonucleotides, sequences of which are described below, were synthesized by phosphoamidite method. The method was carried out in 0.2 μM scale according to a manual of ABI. De-protection of oligonucleotides was carried out with aqueous ammonia at 55° C. for 15–18 hours. Purification was performed by a reverse-phase column of HPLC manufactured by Hitachi.

Oligonucleotide (1) containing a promoter region: this oligonucleotide is composed of a promoter region linked by a linker, and a sequence complementary to nucleotides 313–326 of a thermostable hemolysin of *Vibrio parahaemolyticus* (VP-TDH) gene (SEQ ID NO: 1).

Oligonucleotide (2): an oligonucleotide complementary to nucleotides 179–202 of VP-TDH gene (24 mer) (SEQ ID NO: 2).

Oligonucleotide (3): an oligonucleotide complementary to nucleotides 254–277 of VP-TDH gene (24 mer) (SEQ ID NO: 3). The phosphate radical at the 5'-terminal is labelled with $^{32}P$.

EXAMPLE 1

Amplification Reaction Using Oligonucleotide (1) Containing a Promoter Region and Oligonucleotide (2)

Using oligonucleotide (1) and oligonucleotide (2) from Reference Example 1, amplification reaction of the genome of *Vibrio parahaemolyticus* was carried out to obtain a large amount of RNA. The reaction condition is described below.

Reaction mixture 50 $\mu$l 10 mM Tris-HCl pH8.3

50 mM KCl 6 mM $MgCl_2$ 3 mM $MnCl_2$ 0.6 mM dNTP 1 mM rNTP 20 pmol oligonucleotide (1)

20 pmol oligonucreotide (2)

Tth-DNA polymerase (manufactured by TOYOBO) 60 units

Tth-RNA polymerase (manufactured by EPICENTRE) 2.5 units

Tth-RNase H (manufactured by TOYOBO) 2 units

Reaction:

93° C., 3 min

65° C., 60 min

EXAMPLE 2

Measurement of Synthesized RNA

RNA synthesized in Example 1 was diluted, and the aliquotes of 50 $\mu$l were dot blotted individually on a nylon membrane (GeneScreen plus manufactured by DuPont). As a control, 50 $\mu$l of denatured genome nucleic acid of VP was dot blotted. The nylon membrane was prehybridized in a 100 $\mu$l of solution containing 6×SSC (1×SSC means 0.15 M NaCl, 0.015M sodium citrate (pH7.0)), 5×Denhardt's solution (1×Denhardt's solution means 0.02% Ficoll, 0.02% polyvinylpyrrolidone, 0.02% bovine serum albumin), 1 mM EDTA, 10 $\mu$g of boiled sperm from salmon (mean length is 500 bases), at 60° C. for 1 hour, then the oligomer (3) prepared in Example 1 was added, and hybridization was carried out at 55° C. for 1 hour. The nylon membrane was sufficiently washed in 6×SSC at 55° C., then dried. An X-ray film (New AIF RX manufactured by FUJI) was contacted to the nylon membrane, and exposed at −80° C. for a whole day and night. Quantification of RNA from the photographic sensitivity of the film showed that the RNA was synthesized about $10^6$ times as much as the genome nucleic acid of the control. This result shows that the method of the present invention is effective.

EXAMPLE 3

Example of Amplification from RNA

Amplification Reaction Using Oligonucleotide (1) Containing a Promoter Region and Oligonucleotide (2)

Using oligonucleotide (1) and oligonucleotide (2), amplification of mRNA of *Vibrio parahaemolyticus* was carried out to obtain a large amount of RNA. The reaction condition is shown below.

Reaction mixture 50 $\mu$l 10 mM Tris-HCl pH 8.3

50 mM KCl 6 mM $MgCl_2$ 3 mM $MnCl_2$ 0.6 mM dNTP 1 mM rNTP 20 pmol oligonucleotide (1)

20 pmol oligonucleotide (2)

Tth-DNA polymerase (manufactured by TOYOBO) 60 units

Tth-RNA polymerase (manufactured by EPICENTRE) 2.5 units

Tth-RNase H (manufactured by TOYOBO) 2 units

Reaction: 65° C., 60min

EXAMPLE 4

Measurement of Synthesized RNA

The RNA synthesized in Example 3 was diluted, and quantified the synthesized RNA from the photographic sensitivity according to the same manner as in Example 2. It was shown that the RNA was synthesized about $10^7$ times as much as the control genome nucleic acid of VP. This result shows that the method of the present invention is effective.

EXAMPLE 5

Use of Two Kinds of Enzymes

Amplification Reaction Using Oligonucleotide (1) Containing a Promoter Region and Oligonucleotide (2)

Using oligonucleotide (1) and oligonucleotide (2), amplification of *Vibrio parahaemolyticus* genome was carried out to obtain a large amount of RNA. The reaction condition is shown below.

Reaction mixture 50 $\mu$l 10 mM Tris-HCl pH 8.3

50 mM KCl 6 mM $MgCl_2$ 3 mM $MnCl_2$ 0.6 mM dNTP 1 mM rNTP 20 pmol oligonucleotide (1)

20 pmol oligonucleotide (2)

Tth-DNA polymerase (Reference Example 4) 60 units

Tth-RNA polymerase (manufactured by EPICENTRE) 2.5 units

Reaction: the reaction at 60° C., 20 min and 70° C., 20 min was repeated four times after the reaction at 95° C., 3 min.

EXAMPLE 6

Measurement of Synthesized RNA

The RNA synthesized in Example 3 was diluted, and quantified the synthesized RNA from the photographic sensitivity according to the same manner as in Example 2. It was shown that the RNA was synthesized about $10^6$ times as much as the control genome nucleic acid of VP. This result shows that the method of the present invention is effective.

Reference Example 2

Synthesis of Various Oligonucleotides

Using a DNA synthesizer model 391 (manufactured by ABI), various oligonucleotides, sequences of which are described below, were synthesized by phosphoamidite method. The method was carried out in 0.2 $\mu$M scale according to a manual of ABI. De-protection of oligonucleotides was carried. out with aqueous ammonia at 55° C. for 15–18 hours. Purification was preformed by a reverse-phase column of HPLC manufactured by Hitachi.

Oligonucleotide (1) containing a promoter region: this oligonucleotide is composed of a promoter region linked by a linker, and a sequence complementary to nucleotides 313–326 of a thermostable hemolysin of *Vibrio parahaemolyticus* (VP-TDH) gene (SEQ ID NO: 1).

Oligonucleotide (3): an oligonucleotide complementary to nucleotides 254–277 of VP-TDH gene (24 mer) (SEQ ID NO: 3). The phosphate radical at the 5'-terminal is labelled with $^{32}P$.

Oligonucleotide (4): this oligonucleotide is composed of a promoter region linked by a linker, and an oligonucleotide region complementary to nucleotides 179–202 of VP-TDH gene (SEQ ID NO: 4).

EXAMPLE 7

Amplification Reaction Using Oligonucleotide (1) Containing a Promoter Region and Oligonucleotide (4)

Using oligonucleotide (1) and oligonucleotide (4), amplification of *Vibrio parahaemolyticus* genome was carried out to obtain a large amount of RNA. The reaction condition is shown below.

Reaction mixture 50 μl

- 10 mM Tris-HCl pH 8.3
- 50 mM KCl
- 6 mM $MgCl_2$
- 3 mM $MnCl_2$
- 0.6 mM dNTP
- 1 mM rNTP
- 20 pmol oligonucleotide (1)
- 20 pmol oligonucleotide (4)
- Tth-DNA polymerase (manufactured by TOYOBO) 60 units
- Tth-RNA polymerase (manufactured by EPICENTRE) 2.5 units
- Tth-RNase H (manufactured by TOYOBO) 2 units Reaction:

- 93° C., 3 min
- 65° C., 60 min

EXAMPLE 8

Measurement of Synthesized RNA

The RNA synthesized in Example 7 was diluted, and quantified the synthesized RNA from the photographic sensitivity. It was shown that the RNA was synthesized about $10^9$ times as much as the control genome nucleic acid of VP. This result shows that the method of the present invention is effective.

Reference Example 3

Ribonuclease H Activity Shown by DNA Dependent DNA Polymerase

A cDNA/RNA hybrid was synthesized, using mRNA from Example 3 as a template, oligonucleotide (TDP-2) (SEQ ID NO: 5), and SSII (super script II, manufactured by BRL: M-MLV reverse transcriptase without the ribonuclease). Then, by adding *E. coli* ribonuclease H and Tth DNA polymerase (manufactured by TOYOBO), the RNA was degraded to prepare a single stranded CDNA. A probe complementary to the cDNA was hybridized. The hybridization was carried out using ALP probe (manufactured by TOYOBO, cat. No. PRB004) according to the manufacturer's directions. In detection, quantification was carried out using a color difference calorimeter described in the specification of JP-A 2-227099. The probe did not react with only SSII because the hybrid remained double stranded. However, in case of addition of *E. coli* ribonuclease H and Tth DNA polymerase, the probe reacted without denaturation, which, proved that the hybrid was single stranded. This indicated that Tth DNA polymerase has a ribonuclease H activity.

The reaction condition and the reaction operation are shown below in detail.

Reaction Condition

Template RNA: mRNA of *Vibrio parahaemolyticus* TDH toxin gene

Primer: oligonucleotide (TDP-2)

Reaction mixture:

- 10 mM Tris-HCl pH 8.3
- 75 mM KCl

- 6 mM $MgCl_2$
- 0.4/1.0 mM d/rNTP
- SSII 100 units

Operation: carried out according to table 1 below.

TABLE 1

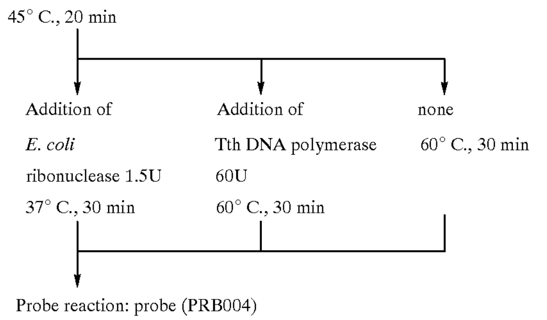

[2 μl of the reaction mixture was spotted on a nylon membrane (Hybond N+, manufactured by Amersham), and measured according to directions of DNA probe manufactured by TOYOBO]

Result: the result is shown in Table 2. 60 units of Tth DNA polymerase showed about a half of 1.5 units of *E. coli* ribonuclease activity.

TABLE 2

| | *E. coli* ribonuclease H | Tth DNA polymerase | none |
|---|---|---|---|
| ΔE | 33.7 | 17.2 | 3.4 |

ΔE: a value reflecting the color and the concentration of pigment of the spot, without unit.

Reference Example 4

Preparation of Ribonuclease H from a Thermophilic Bacterium *Thermus thermophilus*

100 ml of a medium (pH 7.5) containing polypeptone 1.0%, yeast extract 0.5%, NaCl 0.2% was transferred into a 500 ml Sakaguchi flask, and autoclaved at 121° C. for 15 min, then cooled at a room temperature. A loop of *Thermus thermophilus* was inoculated to the medium, and cultured at 70° C. for 24 hours with shaking. Then, 6 L of a medium which has the same compositions was transferred into a 10 L jar fermenter, and autoclaved at 121° C. for 15 min. After allowing to be cooled, 100 ml of the culture liquid above described was added. Culture was carried out at 70° C. for 10 hours, with an aeration rate of 2 L/min and a shaking speed of 400 rpm.

The bacterium was collected from 6 L of the culture liquid by centrifugation (8000 rpm, 10 min), and suspended in a potassium phosphate buffer (pH 7.5) containing 10 mM 2-mercaptoethanol and 5% glycerol (referred as buffer A, hereinafter). Treatment by a sonicator (19 KHz, manufactured by Umigami electric) was carried out for 20 min, and centrifugation was again carried out to remove the debris and collect the supernatant.

After salting-out of the supernatant above mentioned with ammonium sulfate, dialysis against buffer A was carried out. The dialyzed solution was subjected to a chromatography by a Sepharose CL-6B (manufactured by Pharmacia) column equilibrated with buffer A. The enzyme adsorbed to the column. After washing the column with buffer A, elution was performed with buffer A containing 0–1.0 M NaCl. The ribonuclease activity was obtained in a fraction eluted with 0–0.5 M NaCl. The active fraction was dialyzed against buffer A. This solution was subjected to a chromatography by a Phosphocellulose P-11 (manufactured by Whatman) column equilibrated with buffer A to be chromatographed. The enzyme adsorbed to the column. After washing the column with buffer A, elution was performed with buffer A containing 0–1.0 M NaCl. The ribonuclease H activity was obtained in a fraction eluted with 0–0.5 M NaCl.

The active fraction was dialyzed against buffer A. The dialyzed solution was further subjected to a chromatography by a native DNA Cellulose (manufactured by Pharmacia) column equilibrated with buffer A. The enzyme adsorbed to the column. After washing the column with buffer A, elution was performed with buffer A containing 0–1.0 M NaCl. The ribonuclease H activity was obtained in a fraction eluted with 0–0.5 M NaCl.

The active fraction was dialyzed against 10 mM Tris-HCl (pH 7.5), 300 mM KCl, 1 mM DTT, 0.1 mM EDTA, 10% glycerol. The dialyzed solution was further dialyzed against 10 mM Tris-HCl (pH 7.5), 300 mM KCl, 1 mM DTT, 0.1 ml EDTA, 50% glycerol to obtain the enzyme preparation.

Activity of ribonuclease H was determined according to the method described below.

Firstly, reagents A, B, C and D which had the following compositions were prepared.

(Reagents)

A. 100 mM Tris-HCl (pH 8.3)
750 mM calcium chloride
60 mM magnesium chloride
30 mM manganese chloride B. 104 cpm/2 μl poly A/poly dT*

C. 20% trichloroacetic acid (2 mM pyrophosphate)

D. 10 μg/μl BSA

Preparation of the substrate poly A/poly dT labelled with [$^3$H].

100 mg of poly A (manufactured by Pharmacia, code 27-4110-01) was dissolved in 10 ml of sterilized water. 5 units of poly dT (manufactured by Pharmacia, code 27-7834-01) was dissolved in 200 μl of TE buffer. [$^3$H] poly A (manufactured by Amersham: code TRK.480, 10 μCi) was dissolved in 50 μl of the poly A solution previously prepared. To prepare the substrate for 50 samples, [$^3$H] poly A+poly A thus prepared corresponding 500000 cpm was taken out, and mixed with 20 μl of the poly dT solution (19 pmol/μl). 20 μl of 5×buffer for annealing (50 Mm Hepes-KOH (pH 8.0), 500 mM KCl) and 100 μl of sterilized water was added to 100 μl. This solution was heated at 65° C. for 10 min, and cooled at a room temperature. The cooled solution was used as a substrate solution.

Then, 2.5 μl of reagent A, 2 μl of reagent B, and 19.5 μl of sterilized water were added into a microtube. After stirring, 1 μl of the enzyme was added, and reaction was carried out at 60° C. for 20 min, then cooled with ice. 25 μl of reagent D and 50 μl of reagent C were added and stirred. After further cooling of the reaction mixture for 10 min, the acid-insoluble fraction was separated by centrifugation (12000 rpm, 10 min). 50 μl of the acid-soluble fraction of the supernatant was taken out, and counted by a liquid scintillation counter (manufactured by Packard) to determine [$^3$H] liberated. One unit of the enzyme was defined as an amount of the enzyme that liberated 1 μmol of acid-soluble material per minute under this condition.

(1) Molecular weight

Figure 3:
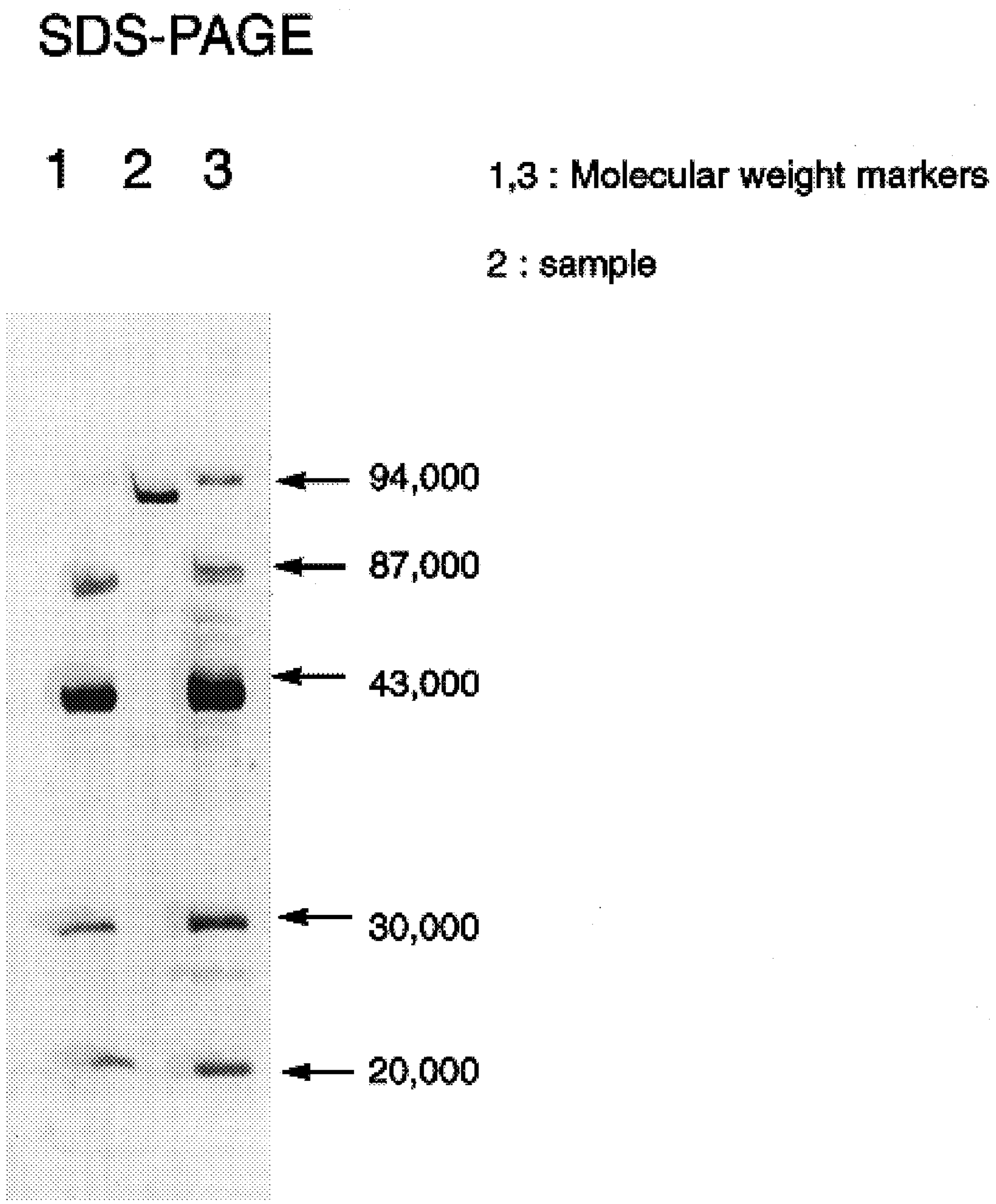
FIG. 3 is a SDS-PAGE pattern of ribonuclease H from *Thermus thermophilus.*

The enzyme preparation above described was applied to electrophoresis with a known molecular weight markers at the same time. Comparing from the known molecular weight markers, the molecular weight of the enzyme was estimated to be 85,000–95,000 (FIG. 3).

(2) Heat Stability

Figure 4:
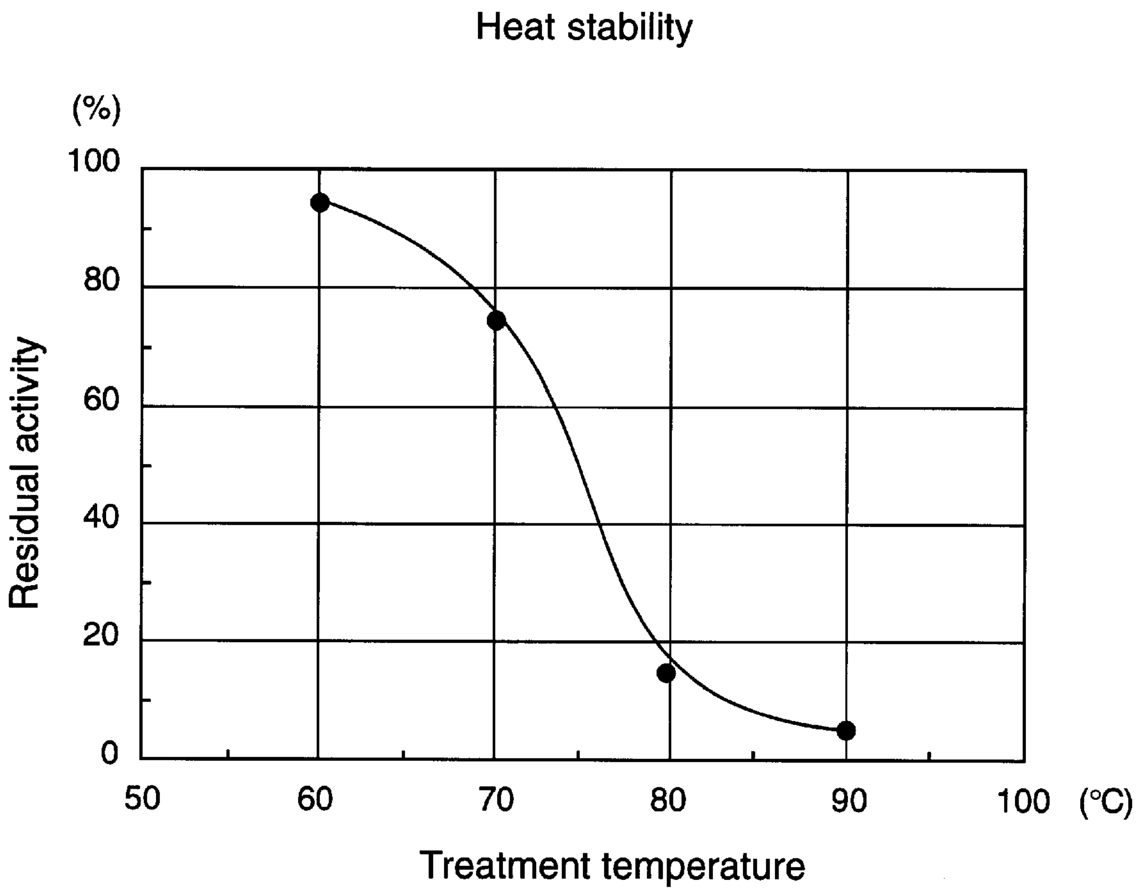
FIG. 4 is a graph showing heat stability of ribonuclease H from *Thermus thermophilus.*

After treatment of the enzyme preparation above described at pH 8.0 and 60° C.–90° C. for 2 hours, the residual activity was measured. The residual activity after the heat treatment was more than 50% of the original activity after treatment at 75° C. for 2 hours (FIG. 4).

(3) Optimal pH

Figure 5:
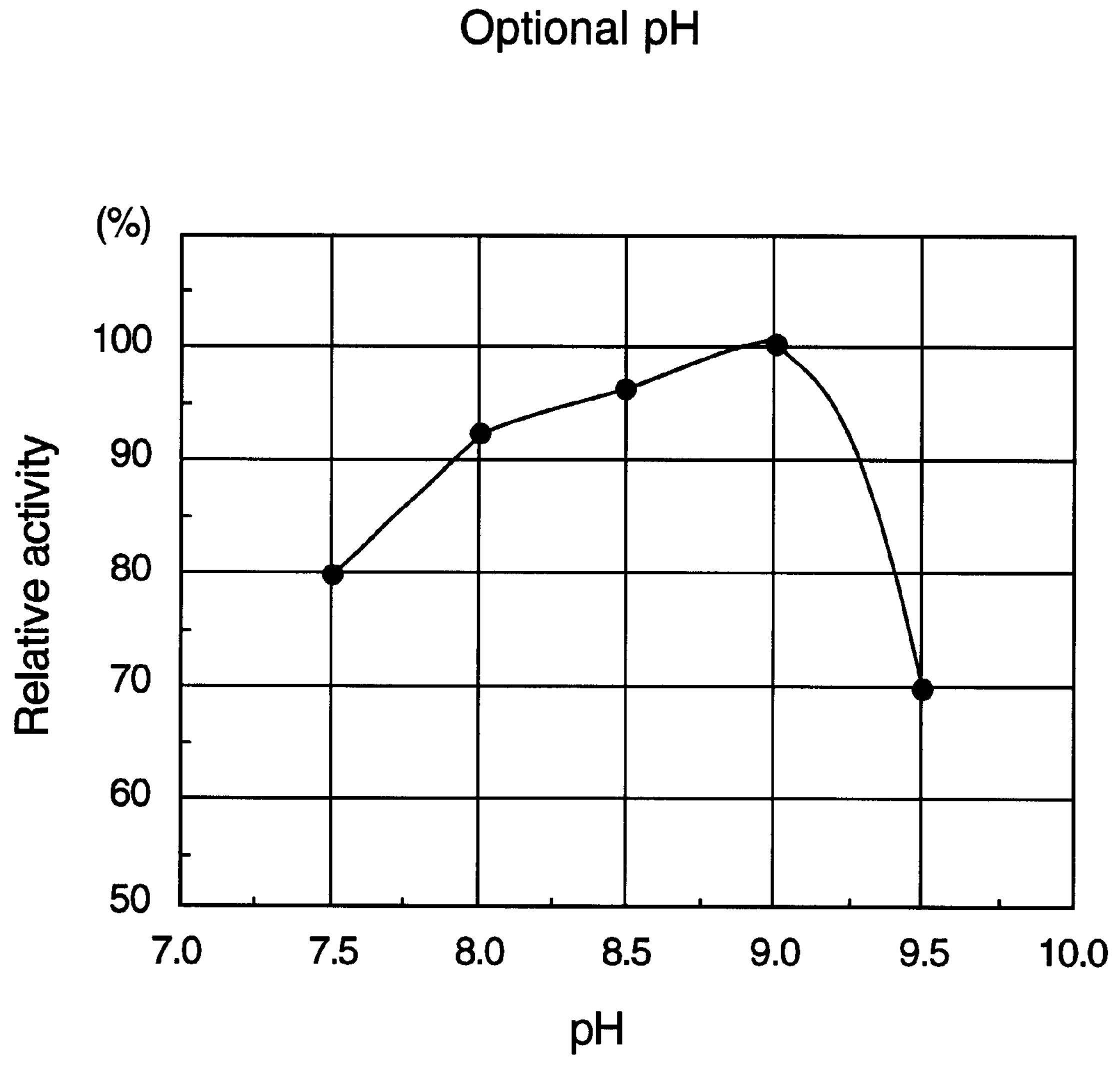
FIG. 5 is a graph showing optimal pH of ribonuclease H from *Thermus thermophilus.*

From the action of the enzyme preparation at pH 7.5–9.5, the optimal pH was determined. Adjustment of the pH was performed by varying the pH of reagent A. The result showed that the optimal pH was about pH 7.5–9.5 (FIG. 5).

(4) DNA Dependent DNA Polymerase Activity

This enzyme had a DNA dependent DNA polymerase activity in addition to the ribonuclease H activity. The DNA dependent DNA polymerase activity was more than about five times of the ribonuclease H activity. As for the DNA dependent DNA activity, one unit was defined to be an amount of the enzyme that incorporated 10 nmol of dTNP into acid-insoluble precipitation using ssDNA/primer as a substrate at 70° C. for 30 min.

(5) RNA Dependent DNA Polymerase (Reverse Transcriptase) Activity

This enzyme had a RNA dependent DNA polymerase (reverse transcriptase) activity in addition to the ribonuclease H activity. The RNA dependent DNA polymerase activity was less than about a tenth of the ribonuclease activity. As for the RNA dependent DNA activity, one unit was defined to be an amount of the enzyme that incorporated 10 nmol of dTTP into acid-insoluble precipitation using poly (A) oligo (dT) as a substrate at 70° C. for 30 min.

What is claimed is:

1. A method for amplifying a target nucleic acid sequence using thermostable enzymes, in which the copy number of the target nucleic acid sequence is increased in a reaction medium comprising magnesium ions and manganese ions at a ratio of about 1:1 to about 4:1 and deoxyribonucleoside and ribonucleoside triphosphates at a ratio of about 1:10 to about 10:1 at a substantially constant temperature, and where an RNA comprises a first template, that comprises the following steps:

Step 1: hybridizing a first primer containing a sequence complementary to a first template RNA and a promoter sequence at the 5' terminal side thereof, with said first template RNA, which contains a target RNA optionally treated by denaturation to render it single-stranded, and elongating said first primer by thermostable RNA-dependent DNA polymerase to obtain a first primer DNA elongation product, which is a second template DNA complementary to said first template RNA;

Step 2: separating said second template DNA from said first template RNA to obtain said second template DNA in single-stranded form by use of a thermostable ribonuclease H, which degrades only RNA of a DNA/RNA hybrid;

Step 3: hybridizing a second primer containing a nucleic acid sequence complementary to said second template DNA with said single-stranded second template DNA and elongating said second primer by thermostable DNA-dependent DNA polymerase to obtain a second primer DNA elongation product complementary to said second template DNA, and thereby producing a double-stranded DNA intermediate containing a promoter sequence that can operate upstream of said target RNA sequence, wherein said nucleic acid sequence of said second primer is homologous to said target RNA sequence;

Step 4: producing a third template RNA containing a sequence complementary to said target RNA sequence of said first template RNA from said double-stranded DNA intermediate, using thermostable DNA-dependent RNA polymerase, which can recognize said promoter sequence, wherein the thermostable DNA dependent RNA polymerase is derived from *Thermus thermophilus;*

Step 5: hybridizing said second primer with said third template RNA in single-stranded form and elongating said second primer by use of thermostable RNA-dependent DNA polymerase to obtain said second primer DNA elongation product, which is a fourth template DNA complementary to said third template RNA;

Step 6: separating said fourth template DNA from said third template RNA to obtain said fourth template DNA in single-stranded form by use of a thermostable ribonuclease H, which degrades only RNA of a DNA/RNA hybrid;

Step 7: hybridizing said first primer with said single-stranded fourth template DNA and carrying out elongation by thermostable DNA-dependent DNA polymerase to obtain a first primer DNA elongation product complementary to said fourth template DNA, and a fourth template DNA elongation product complementary to said promoter sequence of said first primer, and, in such a way, a double-stranded DNA intermediate containing a promoter sequence that can operate upstream of said target RNA sequence is produced, wherein said nucleic acid sequence of said second primer is homologous to said target RNA sequence;

Step 8: increasing the copy number of said third template RNA in single-stranded form containing a sequence complementary to said target RNA sequence of said first template RNA from said double-stranded DNA intermediate using thermostable DNA-dependent RNA polymerase, which can recognize said promoter sequence; and Step 9: optionally repeating said Step 5 through Step 8 as many times as required using said RNA copy, wherein a single thermostable enzyme is used as the thermostable RNA-dependent DNA Polymerase, and the thermostable DNA-dependent DNA polymerase.

2. The method of claim 1, wherein the reaction temperature is between about 50° and about 70° C.

3. The method of claim 1, wherein the thermostable ribonuclease H is derived from *Thermus thermophilus.*

4. The method of claim 1, wherein said method further comprises hybridizing a labeled probe with a single-stranded RNA, a double-stranded DNA or a DNA/RNA hybrid, which is the amplified product of the target nucleic acid sequence described in claim 1, after optional denaturation treatment thereof, and detecting hybridization of the labeled probe.

5. The method of claim 1, wherein said second primer comprises a sequence selected from the group consisting of SEQ ID NO: 6 through SEQ ID NO: 11.

6. A kit for amplifying a specific RNA sequence, which-comprnses:

(a) a first primer containing a sequence complementary to the sequence of a first template, and a promoter sequence at the 5'-terminal side thereof;

(b) a second primer containing a sequence complementary to the sequence of a second template;

(c) thermostable DNA-dependent RNA polymerase derived from *Thermus Therophilus;*

(d) thermostable DNA-dependent DNA polymerase having an RNA-dependent DNA Polymerase activity;

(e) thermostable ribonuclease H;

(f) ribonucleoside triphosphates;

(g) deoxyribonucleoside triphosphates;

(h) magnesium ions; and (i) manganese ions, provided that the sequence of the first primer or the second primer is complementary or homologous to the specific RNA sequence, the ratio of magnesium ions to manganese ions is from about 1:1 to about 4:1, and the ratio of deoxyribonucleoside triphosphates to ribonucleoside triphosphates is from about 1:10 to about 10:1.

7. The kit of claim 6, wherein said kit further comprises in step (b) a second primer containing a sequence complementary to the sequence of a second template, and a promoter sequence at the 5'-terminal side thereof.

8. The kit of claim 6, wherein said kit further comprises potassium ions.

9. The kit of claim 6, wherein the kit further comprises a probe for detection.

* * * * *